United States Patent
Neumann

(10) Patent No.: US 11,894,124 B2
(45) Date of Patent: Feb. 6, 2024

(54) METHODS AND SYSTEMS FOR TIMING IMPACT OF NOURISHMENT CONSUMPTION

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/592,047

(22) Filed: Feb. 3, 2022

(65) Prior Publication Data

US 2022/0172820 A1 Jun. 2, 2022

Related U.S. Application Data

(63) Continuation of application No. 17/106,610, filed on Nov. 30, 2020, now Pat. No. 11,270,789.

(51) Int. Cl.
*G16H 20/60* (2018.01)
*G06N 20/00* (2019.01)

(52) U.S. Cl.
CPC ............. *G16H 20/60* (2018.01); *G06N 20/00* (2019.01)

(58) Field of Classification Search
CPC ........ G16H 10/00–80/00; G06N 3/00–99/007; G06F 1/00–2221/2153
See application file for complete search history.

(56) References Cited

U.S. PATENT DOCUMENTS

| | | | | |
|---|---|---|---|---|
| 8,560,334 | B2 * | 10/2013 | Lahteenmaki | G16H 40/67 705/2 |
| 2011/0009708 | A1 * | 1/2011 | Boyes | G16H 20/60 600/300 |
| 2011/0054928 | A1 * | 3/2011 | Sullivan | G16H 20/60 705/2 |

(Continued)

FOREIGN PATENT DOCUMENTS

| | | | |
|---|---|---|---|
| CN | 111046289 A | * 4/2020 | G06F 16/9535 |
| KR | 10-2043959 | * 11/2019 | G16H 20/60 |

OTHER PUBLICATIONS

Ali et al., "Type-2 fuzzy ontology-aided recommendation systems for IoT-based healthcare," Elsevier—Computer Communications, vol. 119, pp. 138-155. (Year: 2018).*

(Continued)

*Primary Examiner* — Jonathon A. Szumny
(74) *Attorney, Agent, or Firm* — Caldwell Intellectual Property Law

(57) ABSTRACT

A system for timing impact of nourishment consumption, the system including a computing device configured to receive a nutrient profile of a subject, wherein the nutrient profile maps physiological data of the subject to current nutrient levels of the subject, determine, using the nutrient profile, a nourishment consumption program, wherein the nourishment consumption program includes at least an alimentary element, and a time of day for consuming the alimentary element wherein the time of day is determined as a function of the nutrient profile and the current nutrient level of the subject, and provide, to the subject, the nourishment consumption program.

20 Claims, 8 Drawing Sheets

(56) References Cited

U.S. PATENT DOCUMENTS

| | | | | |
|---|---|---|---|---|
| 2012/0094258 A1* | 4/2012 | Langheier | | G16H 20/30 |
| | | | | 434/127 |
| 2013/0004923 A1* | 1/2013 | Utter, II | | A61B 5/11 |
| | | | | 434/127 |
| 2013/0151357 A1* | 6/2013 | Havas | | G06Q 50/12 |
| | | | | 705/15 |
| 2013/0218602 A1* | 8/2013 | Lahteenmaki | | G06Q 10/10 |
| | | | | 705/3 |
| 2014/0088995 A1* | 3/2014 | Damani | | G16H 20/10 |
| | | | | 705/2 |
| 2014/0287384 A1* | 9/2014 | Boyes | | G09B 5/02 |
| | | | | 434/127 |
| 2015/0317453 A1* | 11/2015 | Cunningham | | B65D 83/04 |
| | | | | 700/232 |
| 2016/0357941 A1* | 12/2016 | Wilkinson | | G16H 20/60 |
| 2017/0202802 A1* | 7/2017 | Fernandez | | A61K 31/202 |
| 2017/0249445 A1* | 8/2017 | Devries | | A61B 5/742 |
| 2018/0039759 A1* | 2/2018 | Astigarraga | | G16H 40/63 |
| 2018/0240542 A1* | 8/2018 | Grimmer | | G16H 20/60 |
| 2018/0308390 A1* | 10/2018 | Moser | | A63B 24/0075 |
| 2018/0374385 A1* | 12/2018 | Benefield | | G09B 19/0092 |
| 2019/0027060 A1* | 1/2019 | Ishii | | G06Q 30/02 |
| 2019/0051212 A1* | 2/2019 | Hong | | G16H 20/60 |
| 2019/0145988 A1* | 5/2019 | Haddad | | G16B 40/00 |
| | | | | 514/52 |
| 2019/0221303 A1* | 7/2019 | Bennett | | G16H 10/20 |
| 2019/0295440 A1* | 9/2019 | Hadad | | G06F 40/137 |
| 2020/0194106 A1* | 6/2020 | Olson | | G16H 40/67 |
| 2020/0219605 A1* | 7/2020 | Govindjee | | G16H 20/60 |
| 2020/0387951 A1* | 12/2020 | Khorakiwala | | G06Q 30/0631 |
| 2021/0265034 A1* | 8/2021 | Barrett | | G16H 20/60 |
| 2022/0020472 A1* | 1/2022 | Choura | | G16H 50/20 |

OTHER PUBLICATIONS

Mokdara et al., "Personalized Food Recommendation Using Deep Neural Network," 2018 Seventh ICT International Student Project Conference (ICT-ISPC). (Year: 2018).*

Nezis et al., Towards a Fully Personalized Food Recommendation Tool, AVI '18, May 29-Jun. 1, 2018, Castiglione della Pescala Italy 2018. (Year: 2018).*

* cited by examiner

METHODS AND SYSTEMS FOR TIMING IMPACT OF NOURISHMENT CONSUMPTION

CROSS-REFERENCE TO RELATED APPLICATIONS

This application is a continuation of Non-provisional application Ser. No. 17/106,610, filed on Nov. 30, 2020, and entitled "METHODS AND SYSTEMS FOR TIMING IMPACT OF NOURISHMENT CONSUMPTION", the entirety of which is incorporated herein by reference.

FIELD OF THE INVENTION

The present invention generally relates to the field of nutrient timing. In particular, the present invention is directed to methods and systems for timing impact of nourishment consumption.

BACKGROUND

The detection of the concentration level of metabolites, nutrients, and other analytes in individuals may be vitally important to their health. For example, the monitoring of glucose levels is particularly important to individuals with diabetes or pre-diabetes. People with various conditions may need to monitor nutrient levels to determine when, for instance, medication is needed.

SUMMARY OF THE DISCLOSURE

In an aspect, a system for timing impact of nourishment consumption, the system including a computing device configured to receive a nutrient profile of a subject, wherein the nutrient profile maps physiological data of the subject to current nutrient levels of the subject, determine, using the nutrient profile, a nourishment consumption program, wherein the nourishment consumption program includes at least an alimentary element, and a time of day for consuming the alimentary element wherein the time of day is determined as a function of the nutrient profile and the current nutrient level of the subject, and provide, to the subject, the nourishment consumption program.

In another aspect, a method for timing impact of nourishment consumption, the method including receiving, by a computing device, a nutrient profile of a subject, wherein the nutrient profile maps physiological data of the subject to current nutrient levels of the subject, determining, by the computing device, using the nutrient profile, a nourishment consumption program, wherein the nourishment consumption program includes at least an alimentary element, and a time of day for consuming the alimentary element wherein the time of day is determined as a function of the nutrient profile and the current nutrient level of the subject, and providing, by the computing device, to the subject, the nourishment consumption program.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for timing impact of nourishment consumption. In an embodiment, the system includes a computing device configured to receive physiological data pertaining to a subject and receive a nutrient profile. In an embodiment, computing device may determine nutrient profile data by training a machine-learning model with physiological data. Nutrient profile may include per-subject pharmacokinetics, or metabolism, absorption, distribution, and excretion rates, for a variety of nutrients. Computing device is configured to determine a nourishment consumption program to time consumption based on the nutrient profile. In an embodiment, computing device may provide compatible alimentary elements linked to a scheduling application and use reacting computing to update nutrient profile and consumption timing at defined intervals.

Figure 1:
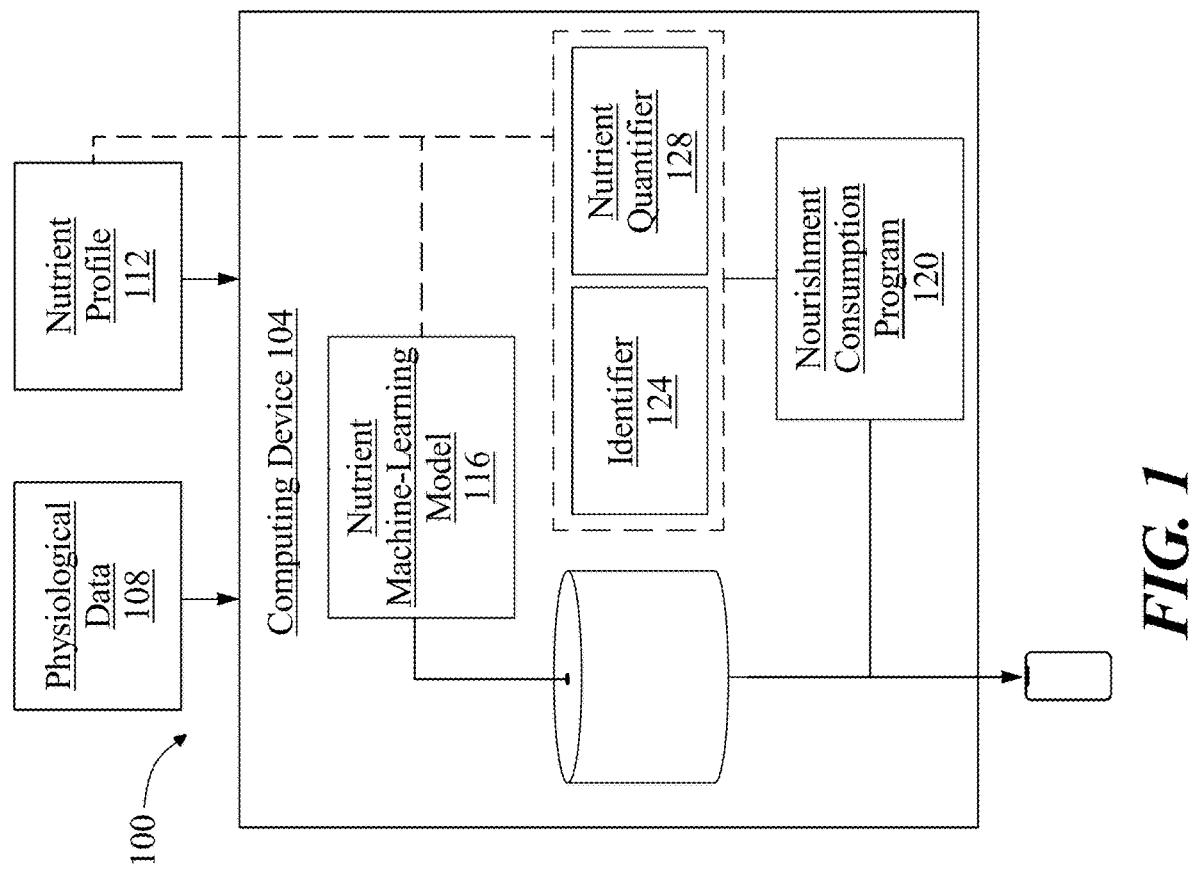
FIG. 1 is a block diagram illustrating a system for timing impact of nourishment consumption.

Referring now to FIG. 1, an exemplary embodiment of a system 100 for timing impact of nourishment consumption is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive physiological data of a subject. A "physiological data," as used in this disclosure, is chemical data, data originating from a biological extraction, medical data, and the like. A biological extraction may include data originating from a physical sample, such as a blood panel, lipid panel, metabolic test, genome sequencing, and the like. Physiological data 108 may include genetic data including the presence of single nucleotide polymorphisms (SNPs), mutations, allele designations (dominant, recessive, +/−, etc.), genetic sequencing data, and the like; epigenetic data including methylation patterns, gene expression patterns, enzyme concentrations, specific activity, circulating RNAs, and the like; microbiome data including gut microbiota, 'good' flora, transient flora, opportunistic pathogens, bacteria, viruses, parasites, fungi, circulating peptides, biologics, and the like; previous medical history including surgeries, treatments, prescriptions, current and past medications, allergies, family history of disease, diagnoses, prognoses, and the like; physiological data including systolic and diastolic blood pressure, resting heart rate, VO2 max, oxygen saturation, blood cell counts, hemoglobin/hematocrit levels, blood iron concentration, body mass index (BMI), blood sugar, HDL/LDL cholesterol levels, hormone levels, and the like; among any other data that one skilled in the art may recognize as physiological data 108 data. Physiological data 108 may include a variety of data, from a variety of sources, with the data originating from the subject and/or a plurality of subjects, and from a variety of categories and sources, for instance and without limitation, as described in U.S. Nonprovisional application Ser. No. 16/886,647, filed on May 28, 2020, and entitled "METHODS AND SYSTEMS FOR DETERMINING A PLURALITY OF BIOLOGICAL OUTCOMES USING A PLURALITY OF DIMENSIONS OF PHYSIOLOGICAL DATA USER DATA AND ARTIFICIAL INTELLIGENCE," the entirety of which is incorporated herein by reference.

Continuing in reference to FIG. 1, physiological data 108 data may correspond to a nutritional need of a subject. A "nutritional need," as used in this disclosure, is a quantity of at least a nutrient and/or of a plurality of nutrients for a subject. Nutrient need may be recommended for subject for maintenance of health, improvement of physiology, addressing a symptom, disease, illness, injury, or any type of malady. Nutrient need may refer to, without limitation, macronutrients, such as protein, including non-essential amino acids, essential amino acids, fats including non-essential fats, essential fats such as long-chain polyunsaturated fatty acids (LC-PUFAs), short-chain polyunsaturated fatty acids (SC-PUFAs), omega fatty acids, carbohydrates, including digestible and non-digestible carbohydrates such as dietary fiber, inulin, *psyllium*, and methylcellulose; micronutrients, such as vitamin A, thiamin (vitamin B1), riboflavin (vitamin B2), niacin (vitamin B3), pantothenic acid (vitamin B5), vitamin B6, biotin (vitamin B7), folate (vitamin B12), vitamin C, vitamin D2, vitamin D3, vitamin E, vitamin K1, vitamin K2; minerals such as calcium, phosphorous, potassium, sodium, magnesium; trace elements such as iron, sulfur, manganese, selenium, chromium, molybdenum, copper, cobalt; halides such a chloride and iodine; electrolytes and salts including bicarbonate, creatine, and phosphocreatine; caloric content, or any other substance that provides nourishment essential for growth and maintenance of subject.

Continuing in reference to FIG. 1, computing device 104 may receive a nutrient profile of the subject, wherein the nutrient profile includes physiological data 108 data mapped to current nutrient levels of the subject. A "nutrient profile," as used in this disclosure, is a profile including any nutrient data corresponding to a subject's current nutrient levels and recommended nutrient levels. Nutrient profile 112 may include subject current nutrient levels as they relate to recommended nutrient levels, for instance as numerical values the indicate the amounts relative to one another. Nutrient levels may correspond to blood serum levels of nutrients of current nutrition, for instance as determined from a physiological data. Nutrient levels may correspond to percent daily recommended values (or recommended values determined on a customized, per-subject basis). A nutrient profile 112 may include qualitative values such as "deficiency", "surplus", "yes", "no", etc., of nutrient levels. A nutrient profile 112 may include quantitative values of nutrient levels such as a numerical values, functions of values, matrices, arrays, vectors, systems of equations, variables, coefficients, metrics, parameters, and the like. A nutrient profile 112 may serve as a "survey" of the current state of nutrition of a subject, including any acute and chronic nutritional deficiencies, nutritional surpluses, recommended and/or calculated nutritional targets, etc.

Continuing in reference to FIG. 1, receiving nutrient profile 112 may include generating a nutrient machine-learning model, using a machine-learning process, wherein the nutrient machine-learning model is trained with training data that includes a plurality of data entries wherein each entry correlates physiological data 108 data to current nutrient levels of the subject. A "machine learning process," as used in this disclosure, is a process that automatically uses a body of data known as "training data" and/or a "training set" to generate an algorithm that will be performed by a computing device/module to produce outputs given data provided as inputs; this is in contrast to a non-machine learning software program where the commands to be executed are determined in advance by a subject and written in a programming language. A nutrient machine-learning model 116 may be generated by training a machine-learning process, algorithm, and/or method, with training data, as described in further detail below.

Continuing in reference to FIG. 1, "training data," as used herein, is data containing correlations that a machine learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, training data may include physiological data 108. Training data may originate from the subject, for instance via a questionnaire and a user interface with computing device 104, providing medical history data, retrieving whole genome sequencing, and the like. Training data may be recorded and transmitted to computing device 104 via a wearable device such as a pedometer, gyrometer, accelerometer, motion tracking device, bioimpedance device, ECG/EKG/EEG data, physiological sensors, blood pressure monitor, blood sugar and volatile organic compound (VOC) monitor, and the like. Training data may originate from an individual other than subject, including for instance a physician, lab technician, nurse, caretaker, psychologist, therapist, and the like. Training data may include biomarkers associated with nutrient amounts and quality of subject nutrition, such as red blood cell (RBC) count. RBC count may be elevated due to dehydration, high testosterone. RBC count may be low due to nutrient deficiencies (iron, vitamin B6, vitamin B12, folate), kidney dysfunction, chronic inflammation, anemia, blood loss, and the like. Training data may include hemoglobin levels, which may be elevated due to dehydration, elevated testosterone, poor oxygen deliverability, thiamin deficiency, insulin resistance. Hemoglobin levels may be deceased due to anemia, liver disease, hypothyroidism, exercise, arginine deficiency, protein deficiency, inflammation nutrient deficiencies (vitamin E, magnesium, zinc, copper, selenium, vitamin B6, vitamin A). Training data may include hematocrit levels which may be elevated due to dehydration, elevated testosterone, poor oxygen deliverability, thiamin deficiency, insulin resistance. Hematocrit levels may be deceased due to anemia, liver disease, hypothyroidism, exercise, arginine deficiency, protein deficiency, inflammation nutrient deficiencies (vitamin E, magnesium, zinc, copper, selenium, vitamin B6, vitamin A). Training data may include mean corpuscular hemoglobin (MCH), or a measure of the average weight of hemoglobin per red blood cell. MCH may be elevated ("macrocytic") due to nutrient deficiencies (vitamin B12, folate, vitamin C), alcohol consumption, thiamin deficiency, and (falsely increased) by hyperlipidemia. MCH may be decreased ("microcytic") due to iron deficiency, nutrient deficiencies (vitamin B6, copper, zinc, vitamin A, vitamin C). Training data may include measures of the average concentration of hemoglobin in red blood cells, which may be elevated ("macrocytic") due to nutrient deficiencies (vitamin B12, folate, vitamin C), alcohol consumption, thiamin deficiency, and (falsely increased) by hyperlipidemia. Concentration of hemoglobin may be decreased ("microcytic") due to iron deficiency, nutrient deficiencies (vitamin B6, copper, zinc, vitamin A, vitamin C). Training data may include data on platelets or small, anucleated cell fragments in blood that are involved in clotting and important for vascular integrity. Platelets may be increased due to iron deficiency anemia, collagen diseases, hemolytic anemia, blood loss, stress, infection, inflammation. Platelets may be decreased due to alcoholism, liver dysfunction, viral/bacterial infections, pernicious anemia, bleeding. Training data may include cellular dimension assessment, such as measures of the average size of platelets, reflecting their function. Platelets counts may be elevated due to increased platelet production, which is often caused by loss or destruction of existing platelets. Elevated mean platelet volume (MPV) may be associated with vascular disease and mortality, certain cancers, type 2 diabetes, and Hashimoto's thyroiditis. MPV may be decreased due to conditions associated with under-production of platelets such as aplastic anemia or cytotoxic drug therapy. Training data may include red blood cell distribution width, a measurement of the variation in red blood cell size. Typically increased due to nutrient deficiency-related anemias (iron, vitamin A, copper, zinc, vitamin B6). Persons skilled in the art, upon review of this disclosure in its entirety, the range of physiological data that may serve as training data to determine nutrient levels of a subject.

Continuing in reference to FIG. 1, training data may include nutritional input data. A "nutritional input," as used in this disclosure, is any nutritional value, nutrient amount, or the like, consumed by the subject. A nutritional input may include any alimentary elements consumed by subject, over any designated period of time. An "alimentary element," as used in this disclosure, is any edible element intended to provide some nutrient value, including hydration, electrolytes, macronutrient, micronutrients, bioactive ingredients, and the like. An alimentary element may include a meal, food item, beverage, supplement, among other items. Persons skilled in the art, upon review of this disclosure in its entirety, the range of nutritional input data, provided by subject or otherwise, that may serve as training data, or input data, in determining nutrient levels of a subject.

Continuing in reference to FIG. 1, computing device 104 may determine the nutrient profile 112 as a function of the nutrient machine-learning model 116. For instance and without limitation, training data may include subject nutritional input (and associated times of consumption) as training data to train nutrient machine-learning model to 'learn', based on the subject's physiological data (age, sex, height, weight, lean body mass, BMI, activity level, basal metabolism, food intolerances, digestive issues, metabolic disorders, etc.), the effect alimentary elements have on nutrient profile 112. Nutrient machine-learning model 116 may identify patterns in the training data the relate to, for instance and without limitation, numerical values that describe current nutrient profile categories.

Continuing in reference to FIG. 1, in non-limiting illustrative examples, training data may include physiological data 108 used to train nutrient machine-learning model 116 to derive pharmacokinetics, or per-subject metabolism, absorption, distribution, and excretion rates, for a variety of nutrients and/or alimentary elements. For instance, training data may include blood concentrations (mg/dL) of nutrients (arginine, glucose, iron, etc.) after meal consumption. Persons skilled in the art may appreciate that training a nutrient machine-learning model with such data, over sufficiently great number of training epochs, for a variety of individual nutrients (or foods) for a variety of alimentary element categories (grains, meats, vegetables, fruits, etc.), may result in rates at which each nutrient may increase/decrease after consuming a meal. In this way, training data may be used to determine a nutrient profile 112 that encompasses per-subject kinetics of nutrient metabolism, absorption, and the like, that may be used to inform consumption timing.

Continuing in reference to FIG. 1, for instance and without limitation, training data may include blood test results from blood draws by a primary physician, or blood analyte results from a wearable device, physiological sensor, or the like. Training data may include nutrient levels for blood analytes, such as vitamin A, glucose, magnesium, and calcium. This data may be used to train the nutrient machine-learning model 116 to derive expected nutrient levels and rates of change of the nutrients (vitamin A, glucose, magnesium, and calcium), provided an input of a consumed alimentary element. In this way, nutrient profile 112 may indicate a numerical value relating to the current nutrient level of 'vitamin A, glucose, magnesium, and calcium' in a subject after consuming 'breakfast', wherein breakfast included 'apple cinnamon oatmeal' and 'whole milk'. The output may include a data structure (nutrient profile 112) that may inform the timing of meals, for instance, based on the 'current nutrient level', the 'target nutrient level', and 'nutrient adsorption rates'.

Continuing in reference to FIG. 1, nutrient profile 112 data may be determined at regular time points and extrapolated for diets. In non-limiting illustrative examples, measuring metabolism and/or absorption rates may be performed using a guiding rubric, for example by learning 'how a ketogenic meal affects blood nutrient levels at 1 hour post-meal, 6 hours post-meal, 24 hours post-meal, etc.'. Alternatively or additionally, training data elements may be collected/recorded and organized for induvial alimentary elements, for instance a fruit, vegetable, and the like. In such an example, inputs may include nutrition facts for an alimentary element, and from the relationships identified (mathematically defined in the model), the expected nutrient level in the subject after consumption can be output. Using this output from nutrient machine-learning model 116, system 100 may determine, based on how these nutrient amounts change over time, 'when' to plan the next meal.

Continuing in reference to FIG. 1, computing device 104 is configured to determine, using the nutrient profile 112, a nourishment consumption program, wherein the nourishment consumption program includes at least an alimentary element and a time of day for consuming the alimentary element. A "nourishment consumption program," as used in this disclosure, is a plan that guides the timing of consumption of a subject and an identity of an item for consumption. Nourishment consumption program 120 may include a time of day for consuming an alimentary element, such as a compatible alimentary element. Nourishment consumption program 120 may include timing the consumption of alimentary elements according to a threshold value of a nutrient. For instance and without limitation, nourishment consumption program 120 may include the timing of meals to keep blood glucose below an upper threshold value, and above a lower threshold value. In such an example, nourishment consumption program 120 may include "when" subject should consume a meal to keep blood sugar within the range, wherein range may include a numerical value range. The timing of consumption may then change depending on the alimentary element considered. For instance, 'times' indicated in the program may be modified as a function of what is consumed. Meals heavy in simple sugars (monosaccharides/disaccharides) may prompt the next meal to follow closely (+1-3 hours); however, if the carbohydrate profile of a meal includes large quantities of complex sugars (starch/fiber), blood sugar may be within range for up to 4-5 hours afterward. Persons skilled in the art may appreciate that determining timing of consumption may be performed with a respect to variety of goals, or targets, diets, etc. For instance, timing can be optimized to achieve a particular amount of macromolecular nutrients (carbohydrates, fats, proteins), calories, micronutrients (iron, calcium, magnesium), to maintain a certain amount bioactive ingredient, to improve/optimize protein synthesis in muscle tissue for recovery from exercise, adherence to a state of ketosis, and the like.

Continuing in reference to FIG. 1, determining the nourishment consumption program 120 may include retrieving an alimentary element program comprising compatible alimentary elements. An "alimentary element program," is a collection of alimentary elements provided to subject. An alimentary element program may include compatible alimentary elements. A "compatible alimentary element," as used in this disclosure, is an alimentary element proscribed to a subject based on the subject's physiological data 108. An alimentary element program may include meals, recipes, grocery items, menu items, supplements, bioactive ingredients, beverages, and the like, that are intended for a subject based on determinations made from physiological data 108 data, such as food allergies and intolerances, improving physiological state of health, decreasing inflammation, addressing chronic nutrient deficiencies, and the like.

Continuing in reference to FIG. 1, compatible alimentary element may include alimentary elements intended to address a nutrition deficiency, reduce inflammation, improve recovery from exercise, improve overall health, among other targeted effects. A compatible alimentary element may include alimentary elements provided as a function of an individual's allergies, food intolerances, philosophical, religions, and lifestyle considerations, among other factors involved. Compatible alimentary element may be generated and provided to a user as a function of a physiological data, such as blood chemistry results, including enzyme concentrations and specific activities for instance of fibrinogen, ferritin, serum amyloid A, α-1-acid glycoprotein, ceruloplasmin, hepcidin, haptoglobin, tumor necrosis factor-α (TNF-α), among other acute phase proteins; for instance cytokine identities and concentrations for instance interleukin-6 (IL-6); blood metabolites identities and concentrations such as blood sugar, LDL and HDL cholesterol content; hormone identities and concentrations such as insulin, androgens, cortisol, thyroid hormones, and the like; erythrocyte sedimentation rate, blood cell counts, plasma viscosity, and other biochemical, biophysical, and physiological properties regarding blood panels, blood tests, and the like, as it relates to biomarkers of inflammation. Compatible alimentary elements may be recommended to a user as a function of these biochemical data with the intention of modifying the biochemical data, for instance by modulating blood sugar, decreasing LDL cholesterol levels, reducing pro-inflammatory biomarkers, minimizing free radicals and oxidative damage, among other targeted effects of alimentary elements on physiological data. For instance, biomarkers of inflammation may include biochemical properties specific to a user such as the level of inflammation as evidence by the presence and concentration of inflammatory biomarkers, post-translational modification of proteins, epigenetic markers, etc., and alimentary elements may be identified and provided to a subject to focus on reducing inflammation for instance and without limitation, as described in U.S. Nonprovisional application Ser. No. 17/007,251 filed Aug. 31, 2020 titled "METHOD AND SYSTEM FOR REVERSING INFLAMMATION IN A USER," the entirety of which is incorporated herein by reference. The level of inflammation, or any biochemical ailment and/or property of a subject may be enumerated, and based on the numerical value, an alimentary element may be recommended to the subject, from which a nourishment consumption program may be defined. Alternatively or additionally, determining nourishment consumption program that improves the user's health state based on the user's biochemistry may be performed, for instance and without limitation, as described in U.S. Nonprovisional application Ser. No. 16/375,303 filed Apr. 4, 2020 titled "SYSTEMS AND METHODS FOR GENERATING ALIMENTARY INSTRUCTION SETS BASED ON VIBRANT CONSTITUTION GUIDANCE," the entirety of which is incorporated herein by reference.

Continuing in reference to FIG. 1, determining the nourishment consumption program 120 may include identifying a compatible alimentary element to address a datum of the nutrient profile 112. Nutrient profile 112 may include a variety of data based on physiological data 108, as described above, such as current nutrient levels, rates of metabolism, adsorption, and nutrient threshold values. A "nutrient threshold," as used in this disclosure, is a numerical value of a nutrient. In non-limiting illustrative examples, nutrient profile 112 may include current levels of water-soluble vitamins, fat-soluble vitamins, minerals, trace elements, blood sugar, cholesterol, lipids, amino acids, phosphocreatine, calories, ATP, rates of extracting each of these nutrients from alimentary elements, and the maximal and minimal nutrient thresholds the subject should maintain. With such data, computing device 104 may identify compatible alimentary elements that may bring subject within the nutrient threshold values and may determine the times of day to initiate consumption of alimentary elements to stay within nutrient thresholds ranges throughout the day-night cycle.

Continuing in reference to FIG. 1, nourishment consumption program 120 may be used to identify a compatible alimentary element to, for instance, address a nutrient deficiency. In non-limiting illustrative examples, computing device 104 may compare nutrient levels in nutrient profile 112 to recommended daily allowance indicated by alimentary element program, and using a mathematical operation such as subtraction, determine if a nutrient deficiency exists. Computing device 104 may match a compatible alimentary element to address the deficiency. Applying the nutrient quantity of an alimentary element may result in a 'nutrient surplus' in which the timing of a subsequent meal may be extended, or a different alimentary element selected altogether. Applying the nutrient quantity may indicate a 'nutrient deficiency' in which case a second alimentary element may be selected to increase the nutrient amount. The quantity may indicate all nutrients are within threshold numerical value ranges, in which case the subject may not need to consume anything for a time.

Continuing in reference to FIG. 1, computing device may calculate a change in the nutrient profile 112 as a function of timing the compatible alimentary element. Computing device 104 may accept an input of a starting value in nutrient profile 112 and a second input of the nutrition facts data of a compatible alimentary element. Computing device 104 may then use the trained nutrient machine-learning model 116 to generate an output of an updated nutrient profile 112. The model may contain relationships regarding the pharmacokinetics of nutrient absorption of macromolecules, micronutrients, etc. The updated nutrient profile 112, which may reflect changes in nutrient levels after consumption, may show nutrients that were obtained, not obtained, an/or depleted. The resulting updated nutrient profile 112 data from using the trained model and the inputs may then inform nourishment consumption program 120, re-calculating the timing of the next meal as nutrient levels change. Persons skilled in the art may appreciate that system 100 may iteratively update nutrient profile 112 at defined intervals, for instance (5 times daily; once an hour, after a meal is eaten), to inform meal timing.

Continuing in reference to FIG. 1, calculating a change in the nutrient profile 112 as a function of timing the compatible alimentary element may include calculating differences in individual nutrient levels in subject. For instance, nutrient profile 112 may include essential amino acid levels for subject as a function of how much protein they have consumed and the protein sources. Computing device 104 may quantify changes in essential amino acid levels after lunch, and use that calculation to best time, to achieve daily recommended amino acid levels, especially for branch chain amino acids (BCAAs). Computing device 104 may select alimentary elements for timing use a mathematical operation, such as addition or subtraction, for instance by adding the amount of protein per serving to the current nutrient levels. Computing device 104 may optimize timing by using a system of equations and/or mathematical expressions to calculate rates (or velocity) of change in the nutrient levels as a function of time. In such an example, the first derivative may be the velocity of reaction (metabolism), second derivative is acceleration (nutrient absorption), and third derivative is the 'jerk', or rate of change of acceleration. The third derivative may refer to 'how long nutrients will continue to increase prior to needing next meal' after eating. Computing device 104 may employ a variety of methods to calculate a change based on relationships identified by nutrient machine-learning model 116. For instance, a multi-variable system of equations, a matrix, vector analysis, series of functions, transforms, derivatives, and the like, may be discovered by nutrient machine-learning model 116 for mapping how nutrient levels change over time, or react to eating a meal, with sufficient physiological data.

Continuing in reference to FIG. 1, calculating a change in the nutrient profile 112 as a function of timing the compatible alimentary element may include calculating differences in individual nutrient levels in subject Timing may be affected by physiological data regarding fitness data, for instance from a fitness tracking application, wearable device, etc.

Continuing in reference to FIG. 1, nourishment consumption program 120 may include a queue of a plurality of compatible alimentary elements, wherein each compatible alimentary element includes an identifier. An "identifier," as used in this disclosure, is a datum of identifiable information relating to a compatible alimentary element. An identifier 124 may include alimentary element name, serving size, price, distributor, restaurant identity, nutrition facts, among other identifiable information for an alimentary element. An identifier 124 may include information necessary for ordering compatible alimentary element, for instance via a mobile application, a web browser, and the Internet etc. An identifier 124 may include information detailing the identity of a compatible alimentary element and perhaps why it is necessary for the subject, how it may improve health, etc. A "queue," as used in this disclosure, is a collection of elements that are maintained in a sequence and can be modified by the addition of entities and removal of elements from the sequence. In non-limiting illustrative examples, the queue may have an "active end" and a "reserve end," wherein the active end is the 'most appropriate compatible alimentary element and time of consuming' to be displayed such as by timing, or some other discriminating criteria; additionally, there may be related alimentary elements that are in the queue "behind" the first active end alimentary element and alternatives nearer the reserve end. In further non-limiting illustrative examples, a user may indicate via a graphical user interface that they do not want an alimentary element, whereby computing device 104 may remove it from the active end and push up by one place the next alimentary elements in the queue. In such an example, computing device 104 may add a newly generated alimentary element to the reserve end to maintain a list that a user may view, scroll through, select/deselect, or the like.

Continuing in reference to FIG. 1, nourishment consumption program 120 may include a time associated with the identifier. A "time," as used in this disclosure, is a datum of chronologically identifiable data used for communicating the timing of consumption. The time may include a time of day, a countdown, or elapsed time for the next alimentary element. Time may include a dynamic time counter, which visibly changes as a function of nutritional input; alternatively or additionally, time may include predetermined times, such as a schedule linked to a calendar. In non-limiting illustrative examples, since each compatible alimentary element may impose a different effect on nutrient profile 112, the identity of each may include a unique time table for consumption.

Continuing in reference to FIG. 1, nourishment consumption program 120 may include a nutrient quantifier for adjusting the nutrient profile 112 as a function of consumption of an alimentary element associated with the identifier. A "nutrient quantifier," as used in this disclosure, is a metric, or instruction, that includes an effect on nutrition for an alimentary element. A nutrient quantifier 128 may include numerical values, for instance, as to which nutrients should decrease after consuming. A nutrient quantifier may include a series of values as a function, for instance, which details how a series of nutrient levels change over time after consuming a particular alimentary element, such as blood sugar and sodium change over a 6 hour period from consuming a cheeseburger. A nutrient quantifier 128 may include an instruction, or logical rule, which dictates how the nutrient profile 112 should be modified from each alimentary element consumed, including how to change the time (to next meal), and which alimentary element identifiers should be added/removed (from queue). Nutrient quantifier 128 may include, in non-limiting illustrative examples, that eating a particular snack+1 hour after consuming a first meal may extend the timing for a second meal for another 3 hours, and perhaps change the identity of the second meal, depending on what the snack provides.

Continuing in reference to FIG. 1, nourishment consumption program 120 may modify identifier 124, time, and nutrient quantifier 128 based on evolutionary considerations such as circadian rhythm, among other considerations. Circadian rhythms are self-sustained approximately 24-hour oscillations in behavior, physiology, and metabolism. These rhythms have evolved to permit organisms to effectively respond to the predictable daily change in the light:dark cycle and the resultant rhythms in food availability encountered in nature. Genetic, epigenetic, biochemical, and physiological studies have revealed more than 10% of expressed genes in any organ exhibit circadian oscillation, and this is seen in liver metabolism, musculoskeletal tissue metabolism, appetite control, blood panel results, etc. These rhythmic transcripts encode key rate-determining steps in neuroendocrine, signaling, and metabolic pathways. Such regulation temporally separates cellular processes and optimizes cellular and organismal fitness. Although the circadian clock is cell-autonomous and has been identified in the majority of tissue types, the circadian system is organized in a hierarchical manner in which the hypothalamic suprachiasmatic nucleus (SCN) of the hypothalamus functions as the master circadian clock (also regulating appetite control) that uses both diffusible and synaptic mechanisms to orchestrate circadian rhythms in the peripheral organs at appropriate phase. For instance, photoreceptive retinal ganglion cells (light harvesting system) send ambient light information to the SCN through monosynaptic connection to ensure that the circadian system is entrained to the daily light:dark cycle. This circadian que, among numerous others, may be reflected in a physiological data 108, for system 100 to accurately determine per-subject circadian rhythm. Nutrient profile 112 may include circadian rhythm dietary patterns, eating timing, sleep cycles, etc. For instance, nutritional input data of subject may be used as an input to determine nourishment consumption program 120 timing, wherein patterns in nutritional input (when a subject eats) may help identify circadian rhythm consumption patterns. Such consumption patterns, reflected in nutrient profile 112, may assist in determining personalized, highly accurate times of day for optimized consumption. Nourishment consumption program 120 may include identifier 124, time, and nutrient quantifier 128, that is based on a circadian rhythm as detailed from nutrient profile 112 of a subject; nutrient machine-learning model 116 may identify and describe relationships in training data that capture per-subject circadian rhythm model of nutrition.

Continuing in reference to FIG. 1, nourishment consumption program 120 may include identifier 124, time, and nutrient quantifier 128 based on cultural considerations such as the standard 3-meal day, diet types and dieting fads, among other considerations. Typical breakfast, lunch, and dinner meals may be difficult to distinguish because skipping meals, snacking, and erratic eating patterns have become more prevalent. Such eating styles may have various effects on cardiometabolic health markers, namely obesity, lipid profile, insulin resistance, blood pressure, heart rate, $VO_2$ max, etc. Nourishment consumption program 120 may include nutrient quantifiers 128 and times aimed at various consumption models such as 'skipping breakfast', 'intermittent fasting', 'decreasing meal frequency' (number of daily eating occasions) and modify timing of consumption based on these paradigms. Consumption patterns may be detailed in nutrient profile 112 or may be collected as inputs via a subject interaction with a user device, such as via a questionnaire provided by a graphical user interface. Furthermore, nourishment consumption program 120 may include program definitions/instructions for meals, snacks, and consumption for use in identifying per-subject consumption patterns to refine nourishment timing more accurately.

Continuing in reference to FIG. 1, providing the nourishment consumption program 120 may include generating, via a graphical user interface, a representation of the nourishment consumption program 120. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the subject and accept input from the subject. Graphical user interface may accept subject input, wherein subject input may include an interaction (such as a questionnaire) with a user device. A user device may include computing device 104, a "smartphone," cellular mobile phone, desktop computer, laptop, tablet computer, internet-of-things (JOT) device, wearable device, among other devices. User device may include any device that is capable for communicating with computing device 104, database, or able to receive, transmit, and/or display nutrient profile 112, nourishment consumption program 120, compatible alimentary elements, etc., for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, etc.), and the like.

Continuing in reference to FIG. 1, providing a representation of the nourishment consumption program 120 may include providing an audiovisual notification. An "audiovisual notification," as used in this disclosure, is an audio and/or visual based notification that may be displayed via an interface with computing device 104. An audiovisual notification may include a prompt to order an alimentary element. An audiovisual notification may include a compatible alimentary element from an alimentary element program. Providing a representation of the nourishment consumption program 120 may include linking, for instance, a subject's calendar application with an alimentary element program. In non-limiting illustrative examples, a user device may be configured to set timed reminders for subject to consume foods, where foods are determined as a function of current location, options, etc.

Continuing in reference to FIG. 1, after providing the nourishment consumption program 120, computing device 104 may update the nutrient profile 112 as a function of subject nutrient consumption. Defined intervals for updating nutrient profile 112 may be set by computing device 104 using reactive computing. "Reactive computing," as used in this disclosure is a declarative programming paradigm that is concerned with data streams and the propagation of change in such data over sampled time period. Reactive computing may also be referred to as "reactive programming." Reactive computing may be used to iteratively sample data inputs and, according to an internal "clock", generate iterative outputs in real-time, as the input data is collected. As used in this disclosure, input data may include nutritional input and/or physiological data 108, for instance as input by subject or collected by a physiological sensor, respectively, and received by computing device 104. As used in this disclosure, output data may include nutrient profile 112 and nourishment consumption program 120. Input data may include data that is generated as training data, and outputs may be from a machine-learning process. Computing device 104 may be configured, using reactive computing, to express static (such as arrays) and/or dynamic (such as event emitters) "data streams" with relative ease, and also communicate an inferred dependence within the associated "execution model" which facilitate the automatic propagation of the changed data flow. For instance, computing device 104 may be configured to employ a trained machine-learning process or model, which describes a mathematical relationship between a particular input to a particular output as the "execution model" to automatically propagate outputs form the incoming signal data. Essentially, computing device 104 may use reactive computing to iteratively receive nutritional inputs and/or physiological data 108 (inputs) and generate nutrient profile 112 and nourishment consumption program 120 (outputs) at regular scheduled intervals, including as data is received (real-time), according to trained machine-learning models such as the nutrient machine-learning model 116. Computing device 104 may use the nutrient profile 112 and an alimentary element program stored in database to generate nourishment consumption program 120 each time nutrient profile 112 is updated throughout the subject's day.

Continuing in reference to FIG. 1, reactive computing may include "model-view-controller" (MVC) architecture, wherein reactive programming may facilitate changes in an underlying model that are reflected automatically in an associated view. For instance, a trained nutrient machine-learning model 116, which may correlate physiological data 108 to nutrient profile 112 data, wherein the nutrient profile 112 may include numerical values for each nutrient. Reactive computing may be performed by computing device 104 using reactive extensions, such as RxJs, RxJAva, RxPy, RxSwift, and other APIs. Reactive computing may be implemented using any type of change propagation algorithm, such as a pull, push, and/or push-pull type approach to data propagation. Reactive computing may be any object-oriented reactive programming (OORP), functional reactive programming (FRP), or the like. Reactive programming may be implemented using for instance rule-based reactive programming languages such as through using relation algebra with Ampersand, Elm, and/or Observable. Persons skilled in the art, upon review of this disclosure in its entirety, will be aware of the various ways in which to implement reactive computing to sample inputs and provide updates in real-time, or at any defined interval.

Figure 2:
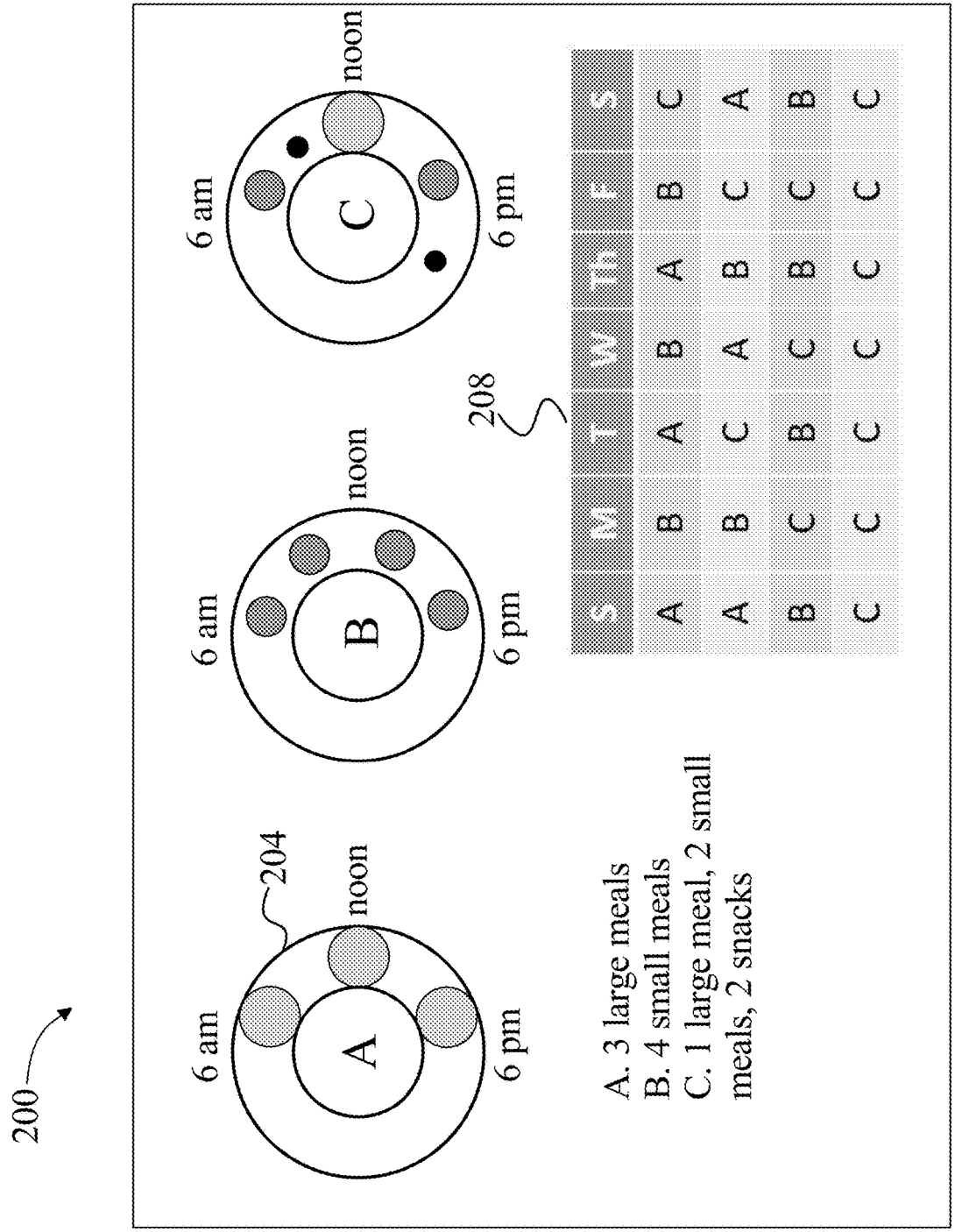
FIG. 2 is a diagrammatic representation of a nourishment consumption program.

Referring now to FIG. 2, a non-limiting exemplary embodiment of nourishment consumption program 120 is illustrated. Nourishment consumption program 120 may include several consumption patterns 204, for instance as designated 'A', 'B', and 'C'. Each may include the timing and designation of meals, snacks, caloric content, etc. Consumption patterns 204 may include daily pattens of nourishment consumption. Consumption patterns may be organized into consumption schedule 208, such as a monthly schedule. Nourishment consumption program 120 may include a variety of consumption patterns 204 organized into consumption schedules 208, for instance based on physiological goals such as lowering BMI, fighting obesity, ameliorating a particular disease (type-2 diabetes), or addressing a symptom (improving sleep deprivation). Nourishment consumption program 120 may include a variety of consumption patterns 204 organized into consumption schedules 208 with particular identified alimentary elements, such as particular grains, meats, fruits, diary, vegetables, and the like, arranged in dietary paradigms such as 'ketogenic diet', 'low glycemic index diet', 'plant-based diet', etc., where the timing of nourishment is guided toward a goal. Such a goal may include maintaining a certain level of iron in the body or keeping cholesterol or blood sugar within a particular range.

Figure 3:
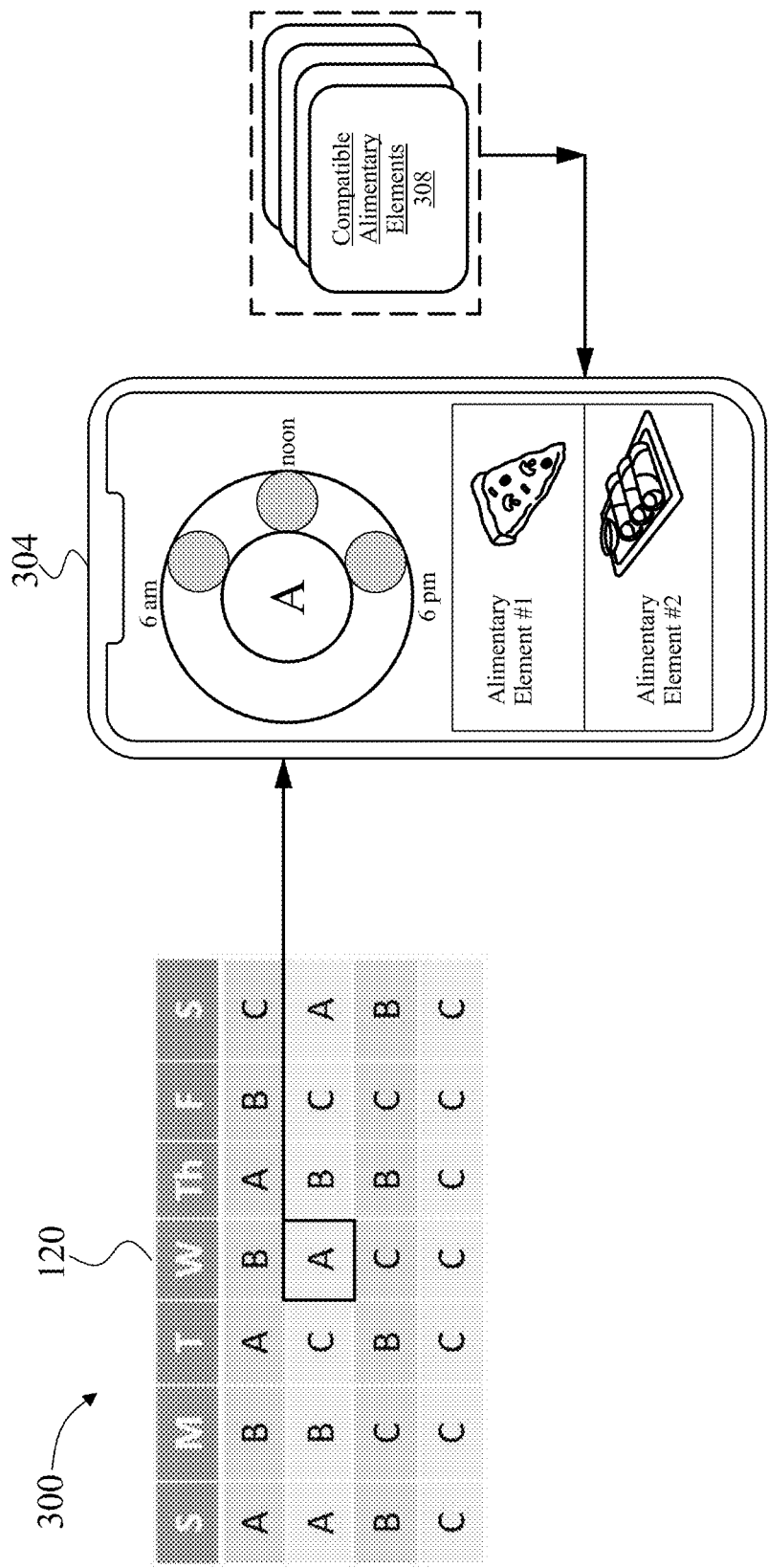
FIG. 3 is a diagrammatic representation of nourishment consumption program on a user device.

Referring now to FIG. 3, a non-limiting exemplary embodiment of nourishment consumption program 120 provided on a user device is illustrated. User device 304 may include computing device 104, a "smartphone," cellular mobile phone, desktop computer, laptop, tablet computer, internet-of-things (IOT) device, wearable device, among other devices. User device may include any device that is capable for communicating with computing device 104, database, or able to receive, transmit, and/or display nutrient profile 112, nourishment consumption program 120, compatible alimentary elements 308. User device 304 may provide a nutrient profile 112, for instance as a collection of metrics determined from physiological data 108 data. User device may provide data concerning average levels of nutrients, nutrient lows, nutrient highs, etc. User device may link timing of foods to preemptive ordering interface for ordering an alimentary element, for instance through a designated mobile application, mapping tool or application, etc. User device may link nourishment consumption program 120 to a scheduling application, such as a 'calendar' feature on user device, which may set timers, alarms, and the like.

Figure 4:
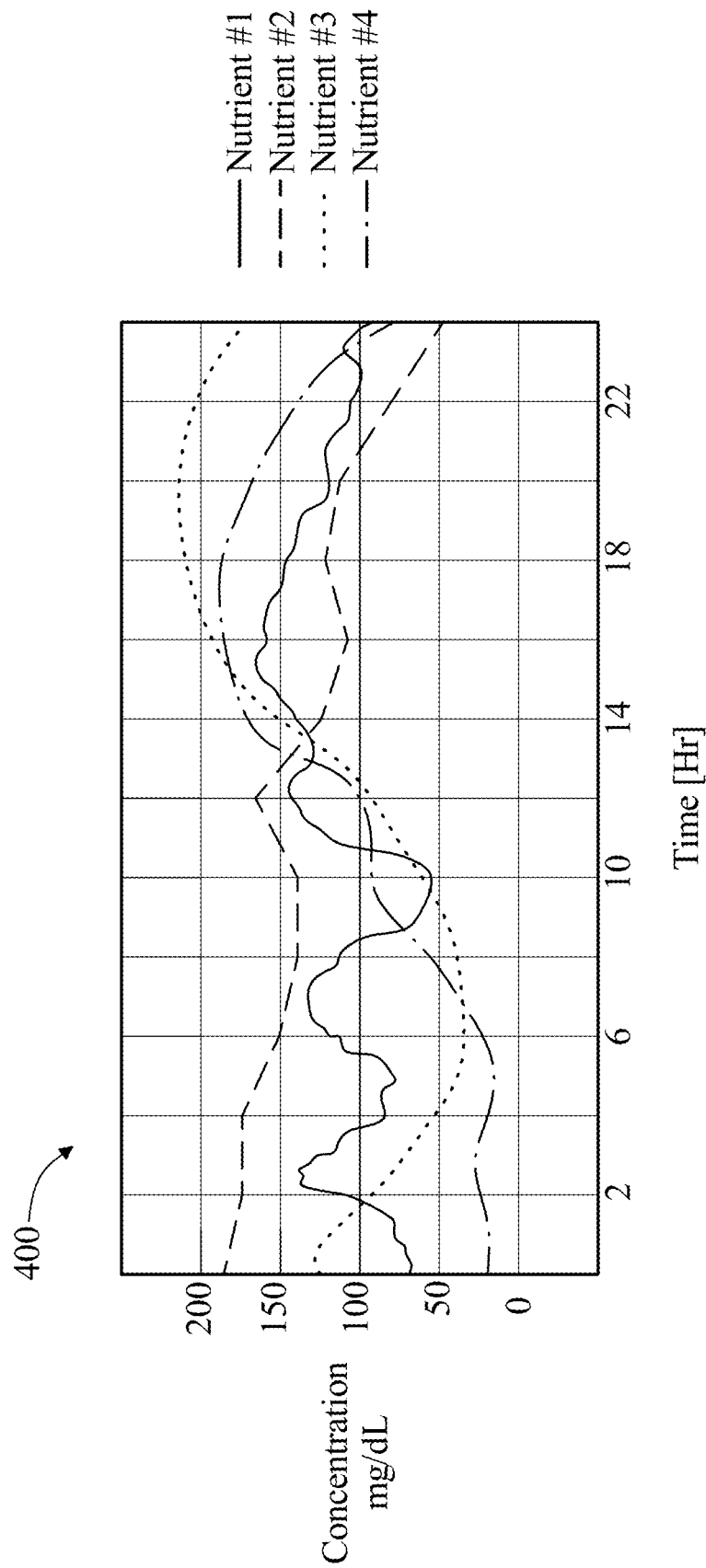
FIG. 4 is a diagrammatic representation of a nutrient profile.

Referring now to FIG. 4, a non-limiting illustrative embodiment of nutrient profile 112 data is illustrated. Physiological data 108 may include data such as blood concentration of nutrients (mg/dL). Computing device 104 may receive physiological data 108, including nutritional input, such as times of meals consumed, and nutrition facts of alimentary elements consumed. Nutrient machine-learning process 116 may determine relationships between consumption of particular alimentary elements and the concentration of nutrient in a physiological data. For instance, as depicted in FIG. 4, nutrient #1 may correspond to blood sugar, which generally oscillates between 50 and 140 mg/dL throughout the day for healthy adults. From time point '0 hour', or 8 am for when subject awakens to approximately '+10 hours' blood sugar remains in normal nutrient threshold values. At approximately, '+10 hours' time, the subject consumes the largest meal of the day, which is diner at approximately 6 pm, and then consumes a nutrient-rich alimentary element approximately 1.5 hours later prior to bed leading to blood sugar between 140 and 199 mg/dL, implying prediabetes without optimal meals and timing. A plurality of nutrients may reach local maxima nutrient amounts during digestion in the evening-night (14-18 hours) if the largest amount of nutrients are consumed during the last few hours awake. Such a pattern may suggest eating smaller meals or spreading nutrients out over a longer time. Inflection points in the function may match to timing of meals. The period after the infection (+1 hour post meal, +2 hours, etc.) may be used to train a machine-learning model to determine rates associated with absorption and metabolism with that subject. Persons skilled in the art may appreciate that performed over sufficiently large periods, and with a large variety of alimentary elements, for a large set of nutrients, nutrient machine-learning model 116 may accurately determine nutrient profile 112 metrics, parameters, numerical values, etc.

Figure 5:
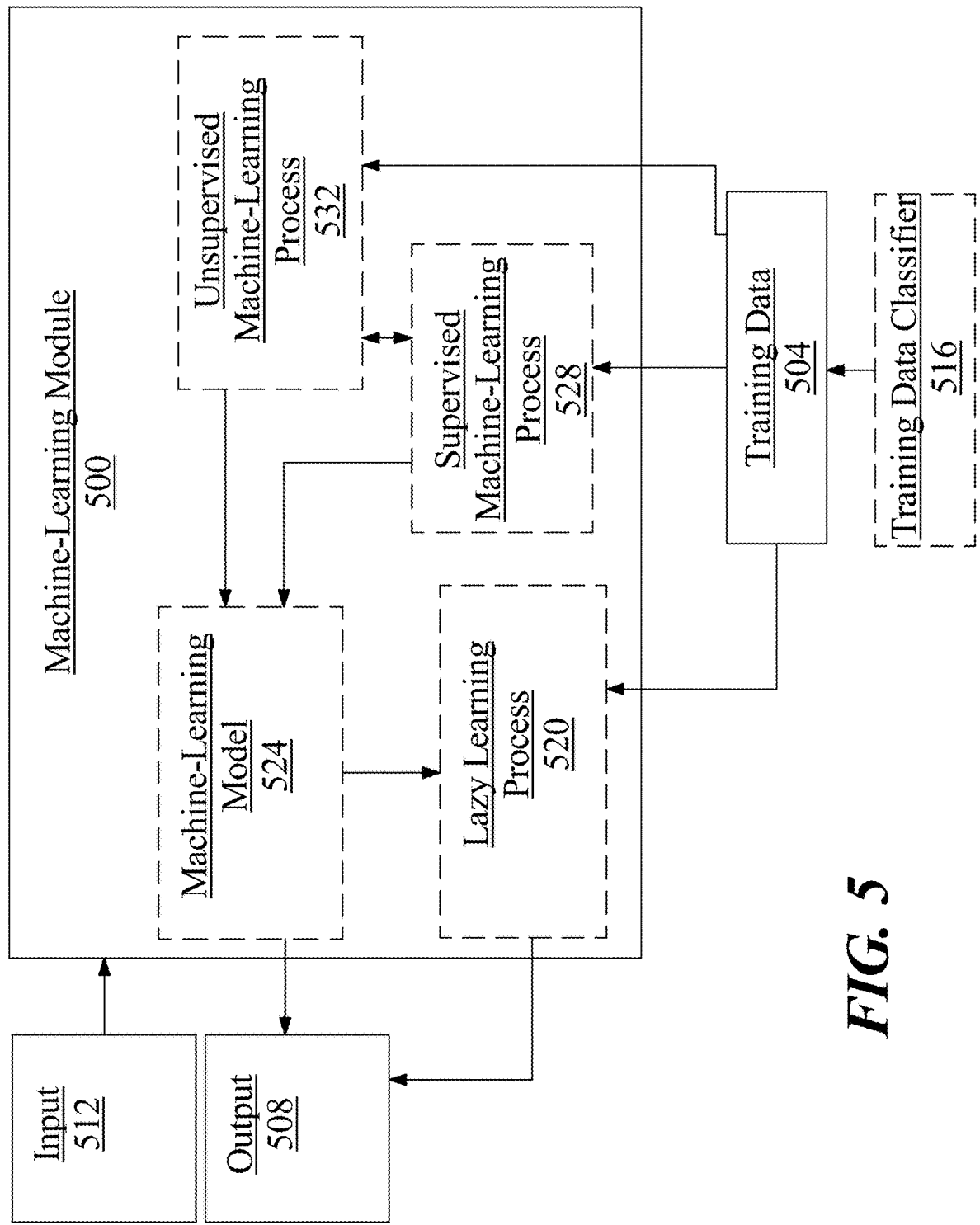
FIG. 5 is a block diagram illustrating an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a subject and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail herein. Training data 504 used by machine-learning module 500 may correlate any input data as described in this disclosure to any output data as described in this disclosure.

Further referring to FIG. 5, training data may be filtered, sorted, and/or selected using one or more supervised and/or unsupervised machine-learning processes and/or models as described in further detail herein; such models may include without limitation a training data classifier 516. Training data classifier 516 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a process whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to elements that characterizes a sub-population, such as a subset of physiological data 108 (such as gene expression patterns as it relates to nutrient profile 112) and/or other analyzed items and/or phenomena for which a subset of training data may be selected.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements, such as classifying physiological data 108 elements nutrient profile 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to nutrient profile 112, as described above, to "learn" the upper and lower limits to the numerical scale, the increments to providing scoring, and the criteria for increasing and decreasing elements encompassed in the nutrient profile 112. A machine-learning model may be used to "learn" which elements of physiological data 108 have what effect on nutrient profile 112, and which elements of nutrient profile 112 are effect by particular alimentary elements and the magnitude of effect, etc.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a nutrient profile 112 (potentially classified into categories), as described above as inputs, nourishment consumption program 120 outputs, and a ranking function representing a desired form of relationship to be detected between inputs and outputs; ranking function may, for instance, seek to maximize the probability that a given input (such as a recommended daily value or dietary goal) and/or combination of elements inputs is associated with a given output (time of day to consume a meal) to minimize the probability that a given input is not associated with a given output, for instance finding the most suitable times to consume meals, and what the meals should be. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning process 532. An unsupervised machine-learning process 532, as used herein, is a process that derives inferences in datasets without regard to labels; as a result, an unsupervised machine-learning process 532 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 5, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 504.

Figure 6:
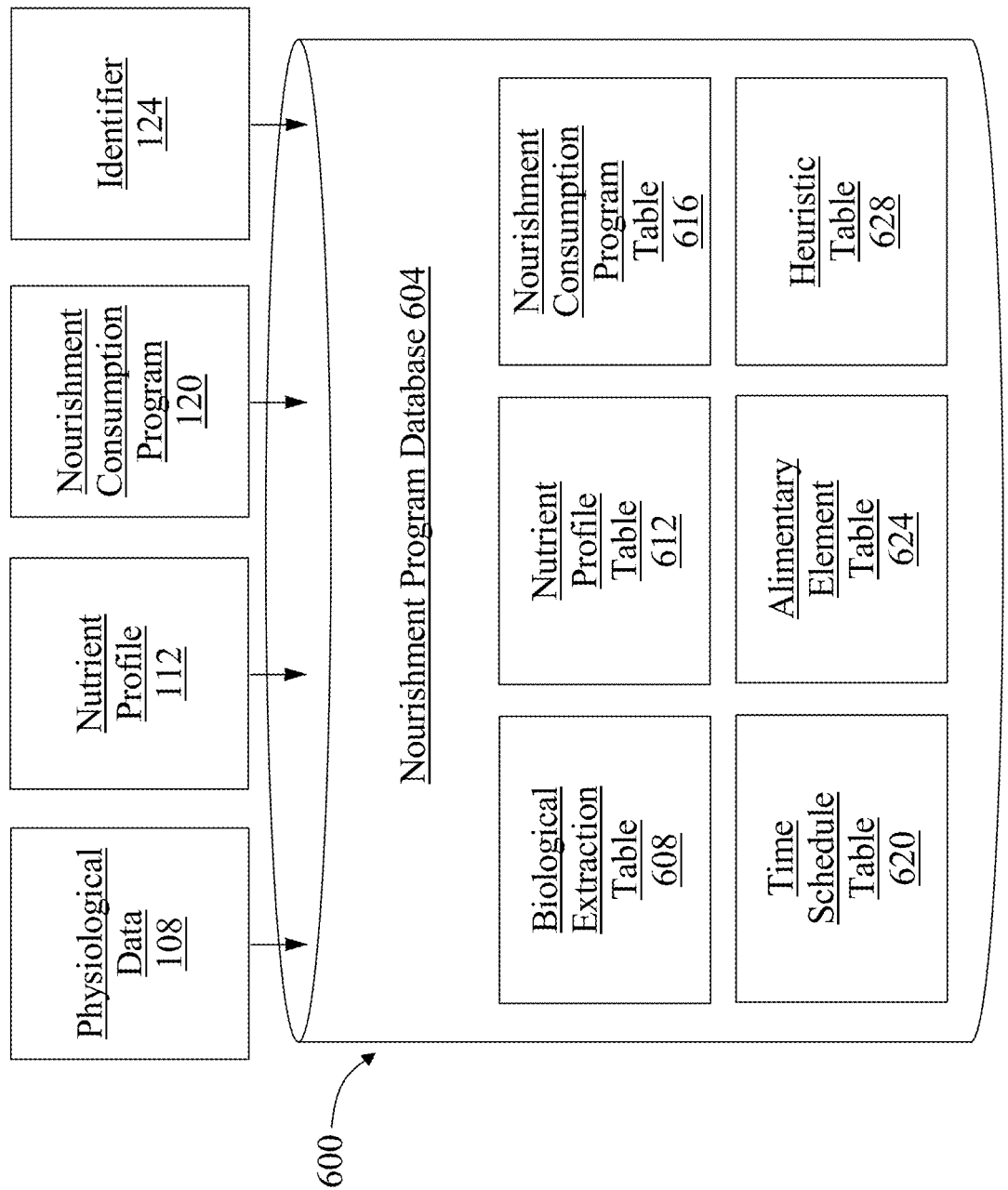
FIG. 6 is a block diagram illustrating an exemplary embodiment of a nourishment program database.

Referring now to FIG. 6, a non-limiting exemplary embodiment 600 of a nourishment program database 604 is illustrated. Physiological data 108 for a plurality of subjects, for instance for generating a training data classifier 516, may be stored and/or retrieved in nourishment program database 604. Physiological data 108 data from a plurality of subjects for generating training data 504 may also be stored and/or retrieved from a nourishment program database 604. Computing device 104 may receive, store, and/or retrieve training data 504, wearable device data, physiological sensor data, and the like, from nourishment program database 604. Computing device 104 may store and/or retrieve nutrient machine-learning model 116, among other determinations, I/O data, models, and the like, in nourishment program database 604.

Continuing in reference to FIG. 6, nourishment program database 604 may be implemented, without limitation, as a relational database, a key-value retrieval database such as a NOSQL database, or any other format or structure for use as a database that a person skilled in the art would recognize as suitable upon review of the entirety of this disclosure. Nourishment program database 604 may alternatively or additionally be implemented using a distributed data storage protocol and/or data structure, such as a distributed hash table and the like. Nourishment program database 604 may include a plurality of data entries and/or records, as described above. Data entries in a nourishment program database 604 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 6, nourishment program database 604 may include, without limitation, physiological data table 608, nutrient profile table 612, nourishment consumption program table 616, time schedule table 620, alimentary element table 624, and/or heuristic table 628. Determinations by a machine-learning process, machine-learning model, ranking function, and/or classifier, may also be stored and/or retrieved from the nourishment program database 604. As a non-limiting example, nourishment program database 604 may organize data according to one or more instruction tables. One or more nourishment program database 604 tables may be linked to one another by, for instance in a non-limiting example, common column values. For instance, a common column between two tables of nourishment program database 604 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 6, in a non-limiting embodiment, one or more tables of an nourishment program database 604 may include, as a non-limiting example, a physiological data table 608, which may include categorized identifying data, as described above, including genetic data, epigenetic data, microbiome data, physiological data, and the like. Physiological data table 608 may include physiological data 108 categories according to metabolism, absorption, etc., categories, and may include linked tables to mathematical expressions that describe the impact of each physiological data 108 datum on nutrient profile 112, for instance threshold values for gene expression, etc., as it relates to nutrient levels. One or more tables may include nutrient profile table 612, which may include data regarding physiological data 108, thresholds, values, categorizations, and the like, that system 100 may use to calculate, derive, filter, retrieve and/or store current nutrient levels, metabolic rates, absorption rates, digestive difficulties, and the like. One or more tables may include nourishment consumption program table 616, which may include data regarding times to eat, identifiers of alimentary elements, schedules, diet types, and the like. Nourishment consumption program table 616 may include data from alike subjects with similar physiological data 108, and the like, that system 100 may use to calculate, derive, filter, retrieve and/or store meal times, for instance timing blood sugar based on meals as a function of alike subjects' meal scheduling. One or more tables may include time schedule table 620, which may include data including times of previous consumption, future scheduled consumption, and the like, that system 100 may use to link to nutrient profile 112 and/or nourishment consumption program 120. One of more tables may include an alimentary element table 624, which may include identifiers and times associated with alimentary elements. One or more tables may include, without limitation, a heuristic table 628, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Figure 7:
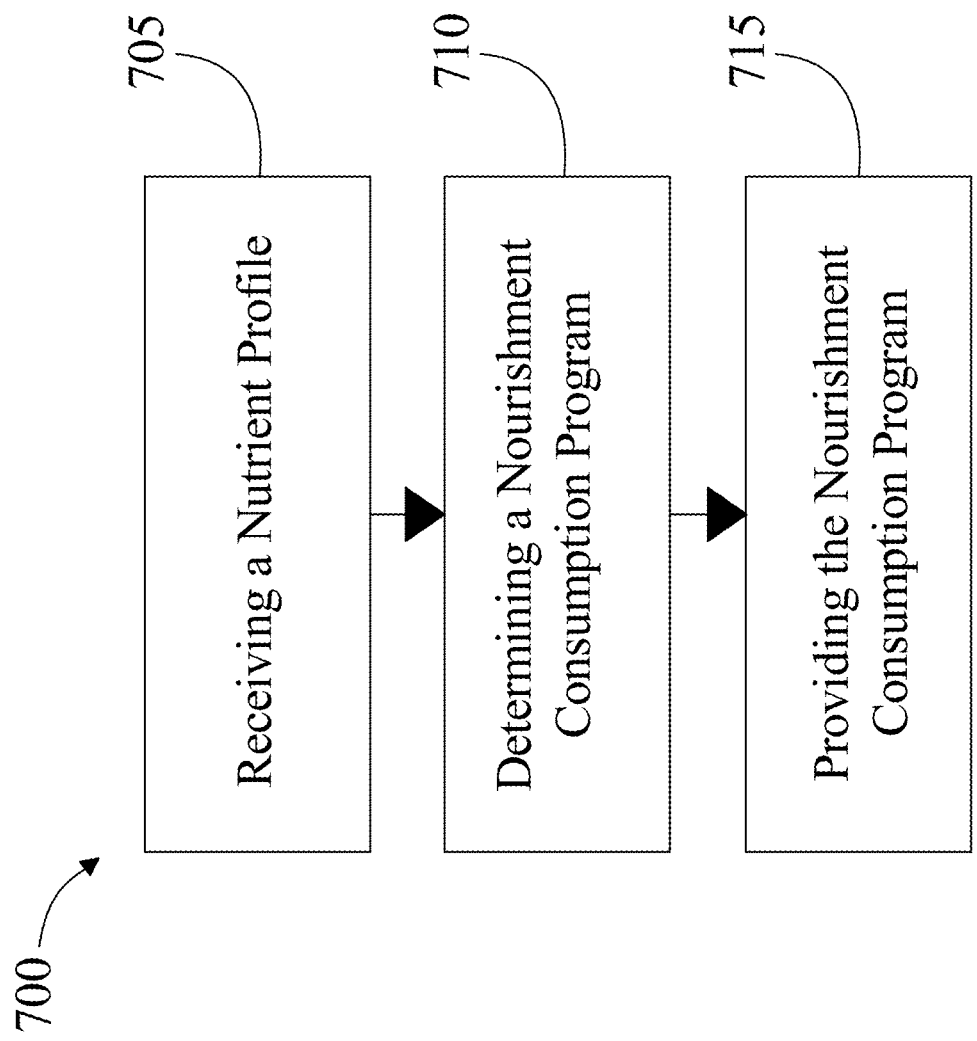
FIG. 7 is a flow diagram illustrating an exemplary workflow of a method for timing impact of nourishment consumption.

Referring now to FIG. 7, an exemplary embodiment 700 of a method for timing impact of nourishment consumption is illustrated. At step 705, computing device 104 is configured for a nutrient profile 112 of a subject, wherein the nutrient profile 112 maps physiological data of the subject to current nutrient levels of the subject. Receiving the nutrient profile 112 may include training a nutrient machine-learning model 116 with training data that includes a plurality of data entries wherein each entry correlates physiological data 108 to current nutrient levels of the subject, and determining the nutrient profile as a function of the nutrient machine-learning model; this may be implemented, without limitation, as described above in FIGS. 1-6.

Still referring to FIG. 7, at step 710, computing device 104 is configured for determining, using the nutrient profile 112, a nourishment consumption program 120, wherein the nourishment consumption program includes at least an alimentary element, and a time of day for consuming the alimentary element wherein the time of day is determined as a function of the nutrient profile 112 and the current nutrient level of the subject. Determining the nourishment consumption program 120 may include retrieving an alimentary element program comprising compatible alimentary elements. Determining the nourishment consumption program 120 may include identifying a compatible alimentary element to address a datum of the nutrient profile 112. Computing device 104 may calculate a change in the nutrient profile 112 as a function of a time of day for consuming the compatible alimentary element. Nourishment consumption program 120 may include a queue of a plurality of compatible alimentary elements, wherein each compatible alimentary element includes an identifier. Nourishment consumption program 120 may include the time of day associated with the identifier, wherein the time of day is selected based on the nutrient profile 112. Nourishment consumption program 120 may include a nutrient quantifier for adjusting the nutrient profile 112 as a function of consumption of an alimentary element associated with the identifier; this may be implemented, without limitation, as described above in FIGS. 1-6.

Continuing in reference to FIG. 7, at step 715, computing device 104 is configured for providing, to the subject, the nourishment consumption program 120. Providing the nourishment consumption program 120 may include generating, via a graphical user interface, a representation of the nourishment consumption program 120. Providing the nourishment consumption program 120 may include updating the nutrient profile 112 as a function of subject nutrient consumption; this may be implemented, without limitation, as described above in FIGS. 1-6.

Continuing in reference to FIG. 7, at step 720, computing device 104 is configured for providing, to the subject, the nourishment consumption program 120. Providing the nourishment consumption program 120 may include generating, via a graphical user interface, a representation of the nourishment consumption program 120. After providing the nourishment consumption program, computing device 104 may update the nutrient profile 112 as a function of subject nutrient consumption; this may be implemented, without limitation, as described above in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
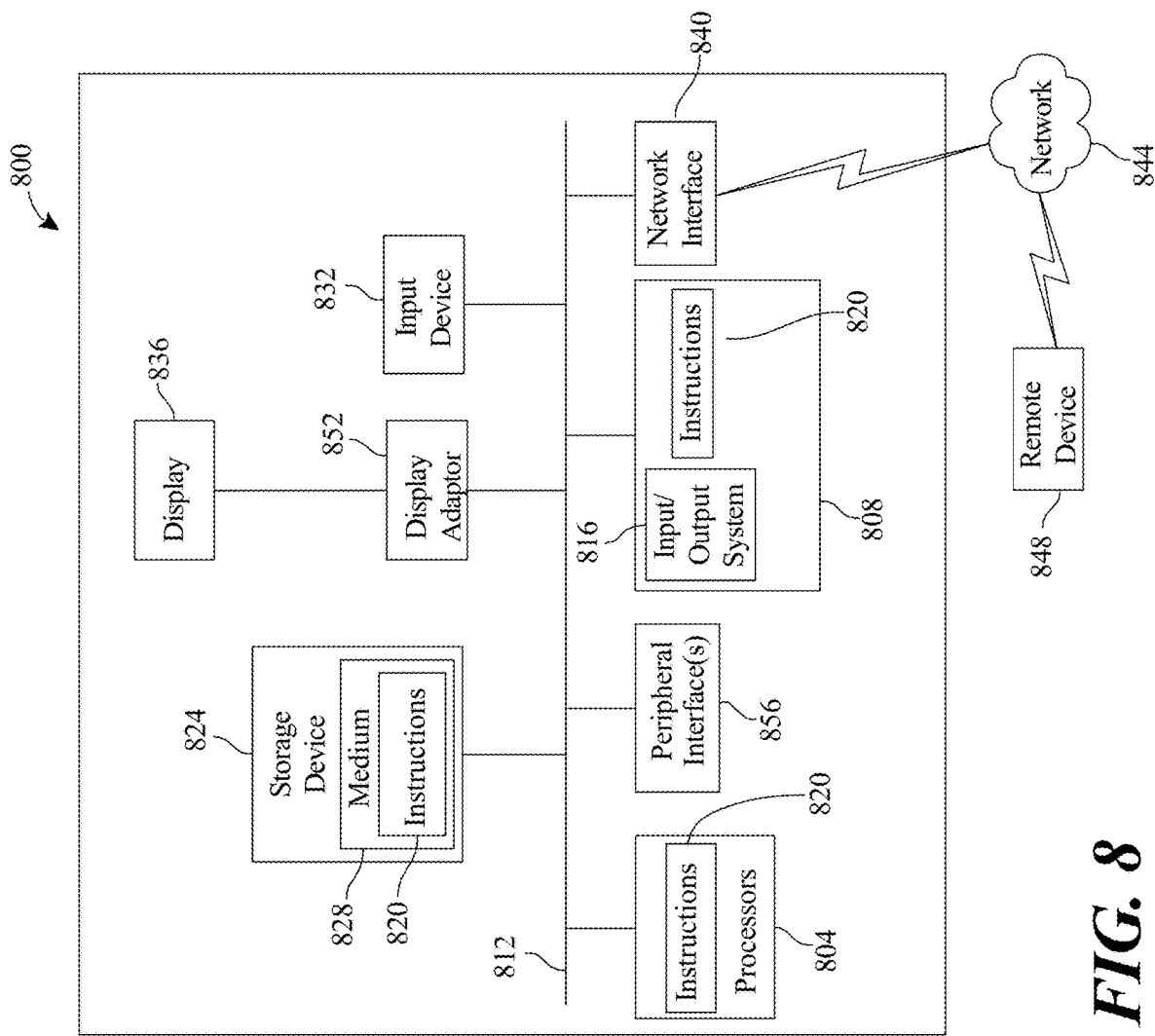
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for timing impact of nourishment consumption, the system comprising:
   a computing device, the computing device configured to:
      receive training data comprising physiological data, correlated to current nutrient levels of a subject, wherein physiological data comprises food intolerances of a subject;
      train a nutrient machine-learning model using the training data;
      generate a nutrient profile of the subject utilizing the nutrient machine-learning model, wherein the nutrient machine-learning model is configured to:
         receive a nutritional input;
         determine relationships between consumption of particular alimentary elements and the concentration of nutrients in physiological data; and
         output the nutrient profile comprising a nutritional deficiency;
      determine, using the nutrient profile, a nourishment consumption program,
      wherein the nourishment consumption program includes:
         at least an alimentary element; and
         a consumption pattern for consuming the at least an alimentary element, wherein:
            the consumption pattern includes a time of day; and
            the time of day is determined as a function of the nutrient profile and the current nutrient levels of the subject;
      provide, to the subject, the nourishment consumption program, wherein providing the nourishment consumption program further comprises:
         providing a representation of the nourishment consumption program to a user device of the subject in the form of an audiovisual notification;

linking the nourishment consumption program to a calendar application of the user device of the subject; and setting timed reminders on the user device of the subject to consume at least one alimentary element as a function of a current location of the subject;

determine defined time intervals using reactive computing, wherein the reactive computing comprises a model-view-controller architecture;

receive a set of nutrition consumption data of the subject as a function of the nourishment consumption program;

generate, using the reactive computing, an updated nutrient profile as a function of the set of nutrition consumption data and the defined time intervals; and provide, to the subject, an updated consumption pattern of the nourishment consumption program as a function of the set of nutrition consumption data and the updated nutrient profile at each defined time interval.

2. The system of claim 1, wherein providing an updated consumption pattern further comprises:

receiving updated training data correlating nutrient consumption data to consumption patterns;

training the nutrient machine-learning model with the updated training data, wherein the nutrient machine-learning model is configured to input nutrient consumption data and output consumption patterns; and determine, using the nutrient machine-learning model, an updated consumption pattern of the nourishment consumption program.

3. The system of claim 1, wherein the nourishment program further comprises a second consumption pattern for consuming a second alimentary element.

4. The system of claim 3, wherein the consumption pattern is updated as a function of the second consumption pattern for consuming the second alimentary element.

5. The system of claim 1, wherein the consumption pattern is determined as a function of a circadian rhythm of the subject.

6. The system of claim 1, wherein the consumption pattern is determined as a function of a nutrient threshold.

7. The system of claim 1, wherein the consumption pattern is determined as a function of cultural considerations of the subject.

8. The system of claim 1, wherein the consumption pattern includes a nutrient consumption frequency.

9. The system of claim 1, wherein the consumption pattern is updated as a function of a nutrient concentration of the subject.

10. The system of claim 1, wherein the computing device is further configured to calculate a change in the nutrient profile as a function of timing a compatible alimentary element.

11. A method for timing impact of nourishment consumption using a computing device, the method comprising:

receiving, by a computing device, training data comprising physiological data, correlated to current nutrient levels of a subject, wherein physiological data comprises food intolerances of a subject;

training, by the computing device, a nutrient machine-learning model using the training data;

generating, by the computing device, a nutrient profile of the subject utilizing the nutrient machine-learning model, wherein the nutrient machine-learning model is configured to:

receive a nutritional input;

determine relationships between consumption of particular alimentary elements and the concentration of nutrients in physiological data; and output the nutrient profile comprising a nutritional deficiency;

determining, using the nutrient profile, a nourishment consumption program, wherein the nourishment consumption program includes:

at least an alimentary element; and a consumption pattern for consuming the at least an alimentary element, wherein:

the consumption pattern includes a time of day; and the time of day is determined as a function of the nutrient profile and the current nutrient levels of the subject;

providing, to the subject, the nourishment consumption program, wherein providing the nourishment consumption program further comprises:

providing a representation of the nourishment consumption program to a user device of the subject in the form of an audiovisual notification;

linking the nourishment consumption program to a calendar application of the user device of the subject; and setting timed reminders on the user device of the subject to consume at least one alimentary element as a function of a current location of the subject;

determining, by the computing device, defined time intervals using reactive computing, wherein the reactive computing comprises a model-view-controller architecture;

receiving a set of nutrition consumption data of the subject as a function of the nourishment consumption program;

generating, by the computing device using the reactive computing, an updated nutrient profile as a function of the set of nutrition consumption data and the defined time intervals; and providing, to the subject, an updated consumption pattern of the nourishment consumption program as a function of the set of nutrition consumption data and the updated nutrient profile at each defined time interval.

12. The method of claim 11, wherein providing an updated consumption pattern further comprises:

receiving updated training data correlating nutrient consumption data to consumption patterns;

training the nutrient machine-learning model with the updated training data, wherein the nutrient machine-learning model is configured to input nutrient consumption data and output consumption patterns; and determine, using the nutrient machine-learning model, an updated consumption pattern of the nourishment consumption program.

13. The method of claim 11, wherein the nourishment consumption program further comprises a second consumption pattern for consuming a second alimentary element.

14. The method of claim 13, wherein the consumption pattern is updated as a function of the second consumption pattern for consuming the second alimentary element.

15. The method of claim 11, wherein the consumption pattern is determined as a function of a circadian rhythm of the subject.

16. The method of claim 11, wherein the consumption pattern is determined as a function of a nutrient threshold.

17. The method of claim 11, wherein the consumption pattern is determined as a function of cultural considerations of the subject.

18. The method of claim 11, wherein the consumption pattern includes a nutrient consumption frequency.

19. The method of claim 11, wherein the consumption pattern is updated as a function of a nutrient concentration of the subject.

20. The method of claim 11, wherein the method further comprises calculating, by the computing device, a change in the nutrient profile as a function of timing a compatible alimentary element.

* * * * *